United States Patent [19]

Frazer

[11] Patent Number: Plant 7,633

[45] Date of Patent: Aug. 27, 1991

[54] AGLAONEMA PLANT NAMED 170-1

[75] Inventor: Edwin J. Frazer, P.O. Box 200, Brisbane, Queensland, Australia, 4069

[73] Assignee: Edwin J. Frazer, Kenmore, Australia

[21] Appl. No.: 515,115

[22] Filed: Apr. 27, 1990

[51] Int. Cl.[5] ..... A01H 5/00

[52] U.S. Cl. ..... Plt./88

[58] Field of Search ..... Plt./88

*Primary Examiner*—James R. Feyrer

*Attorney, Agent, or Firm*—Foley & Lardner

[57] ABSTRACT

An Aglaonema plant named 170-1, having relatively small, narrow leaves, excellent branching, attractive dark and light green variegated leaves, and relatively short habit.

1 Drawing Sheet

The present invention comprises a new and distinct cultivar of Aglaonema hybrida known by the cultivar name 170-1.

The new cultivar is a product of a planned breeding program carried out by the inventor Edwin J. Frazer, P.O. Box 200, Kenmore, Queensland, Australia 4069. The female parent was a cultivar of *Aglaonema commutatum* known by the varietal name Malay Lady, and the pollen parent was a cultivar of *Aglaonema curtisii* named Big. The new cultivar was discovered from the progeny of the stated cross by Edwin J. Frazer in Kenmore, Queensland, Australia. Asexual propagation by division and tissue culture was used to increase the number of plants for evaluation, and has demonstrated the stability of the combination of characteristics of the new cultivar from generation to generation.

The following observations, measurements and values describe plants grown in Palmdale, Fla. under greenhouse conditions which closely approximate those generally used in horticultural practice.

The following traits have been repeatedly observed to be characteristics which in combination distinguish Aglaonema 170-1 from other Aglaonema of the same general type. The characteristics are described by reference to the well known cultivar Maria, the closest comparison cultivar.

1. 170-1 has smaller and narrower leaves than Maria.
2. 170-1 branches more freely than Maria.
3. The leaf color of 170-1 is not as dark as Maria.
4. 170-1 is shorter than Maria.

The accompanying color photograph comprises a front view of a typical plant of 170-1, grown in a six inch pot. Colors are depicted as accurately as possible with color illustrations of this type.

All color references are to the Royal Horticultural Society Colour Chart. Color values are as close as possible, but are approximate as color depends on horticultural practices such as temperature, light conditions and fertilization rate, among others.

Origin: Seedling.

Classification: *Aglaonema hybrida* cv. 170-1.

Propagation: Asexual reproduction either by tissue culture or division.

Plant: In a 6 inch pot, 170-1 is approximately 16 cm. to 20 cm. from the soil surface to the junction of the petioles of the last two (2) unrolled leaves, and approximately 35 cm. to 40 cm. in width after approximately 48 weeks to 54 weeks under appropriate growing conditions from division. All measurements are based on the above parameters.

Stem:

*Growth pattern.*—The stem is erect in growth and is approximately 1.1 cm. to 1.4 cm. in diameter five (5) cm. above the soil surface. Internode distance is approximately 1.3 cm. to 1.5 cm. three (3) cm. above the soil.

*Color.*—The stem is darker than 139A in color.

Petiole: The following information is based on the third expanded leaf from the apex.

*Growth pattern.*—The petiole has fleshy edges extending from the midrib which will be referred to as wings. The wings are approximately 4 mm. to 6 mm. wide at the midpoint of the wing, and extend from the base of the petiole to within approximately 9 cm. to 11 cm. of the leaf base. The apex of the wings is acuminate. The petiole follows the stem axis but diverges from the axis approximately 1 cm. to 3 cm. from the leaf base, forming a horizontal distance from the edge of the stem to the leaf base of approximately 2 cm to 3 cm.

*Physical dimensions.*—The petiole is straight from its base to near the base of the leaf where it will curve away from the stem. The petiole is approximately 4 mm. to 6 mm. in diameter one-half (½) way between the top of the wing and the base of the leaf. The petiole is approximately 12 cm. to 14 cm. in length.

*Color.*—The petiole wings are lighter in color than the midrib, with the midrib being 137C.

Leaf:

*Growth pattern.*—The leaf is ovate with an acuminate apex and an obtuse base. The margin is entire. The leaf is asymmetric, with the side of the leaf unrolling first having less surface area and fewer undulations on the leaf margin than the side unrolling last. The leaf is oriented parallel to the stem axis at the time of full unrolling, changing to 45° to the stem axis as more leaves unroll above it. The midrib is flat over the length of the leaf. The leaf blade is flat from the midrib to the margin.

*Physical dimensions.*—For the pot size and growing time indicated, an average sized leaf is approximately 19 cm. to 22 cm. long and approximately 6 cm. to 7 cm. wide. The leaf is moderately thick.

*Midrib.*—The midrib is thick and 137A in color on the upper side and 137B in color on the under side.

*Primary veins.*—The primary veins are sunken into the upper side and protrude out of the under side. The primary veins are the same color as the leaf tissue surrounding them.

*Color and pattern.*—The leaf is bicolor on the upper side, with a dark background area and lighter irregular bars extending from the midrib to near the edge of the leaf. New leaves on the upper surface have a base or background color of approximately 137A, with the lighter irregular area being between 138B and 138C. Older leaves have a base background color between 139A and 131A, with the lighter, irregular area being between 191A and 191B. The under side color of both new and old leaves is 137B.

Axillary breaks: There is approximately 3 to 5 axillary breaks, with at least one (1) leaf expanded. Leaves will show true color and pattern by the first leaf.

Inflorescence: Not commercially significant.

Roots: Thick white roots with finer laterals.

General observations: Aglaonema 170-1 is a faster growing, more freely branching, and smaller leaved variety than Maria. The smaller leaves and greater branching permits 170-1 to be finished in a smaller pot than Maria.

I claim:

1. A new and distinct cultivar of Aglaonema plant named 170-1, as illustrated and described.

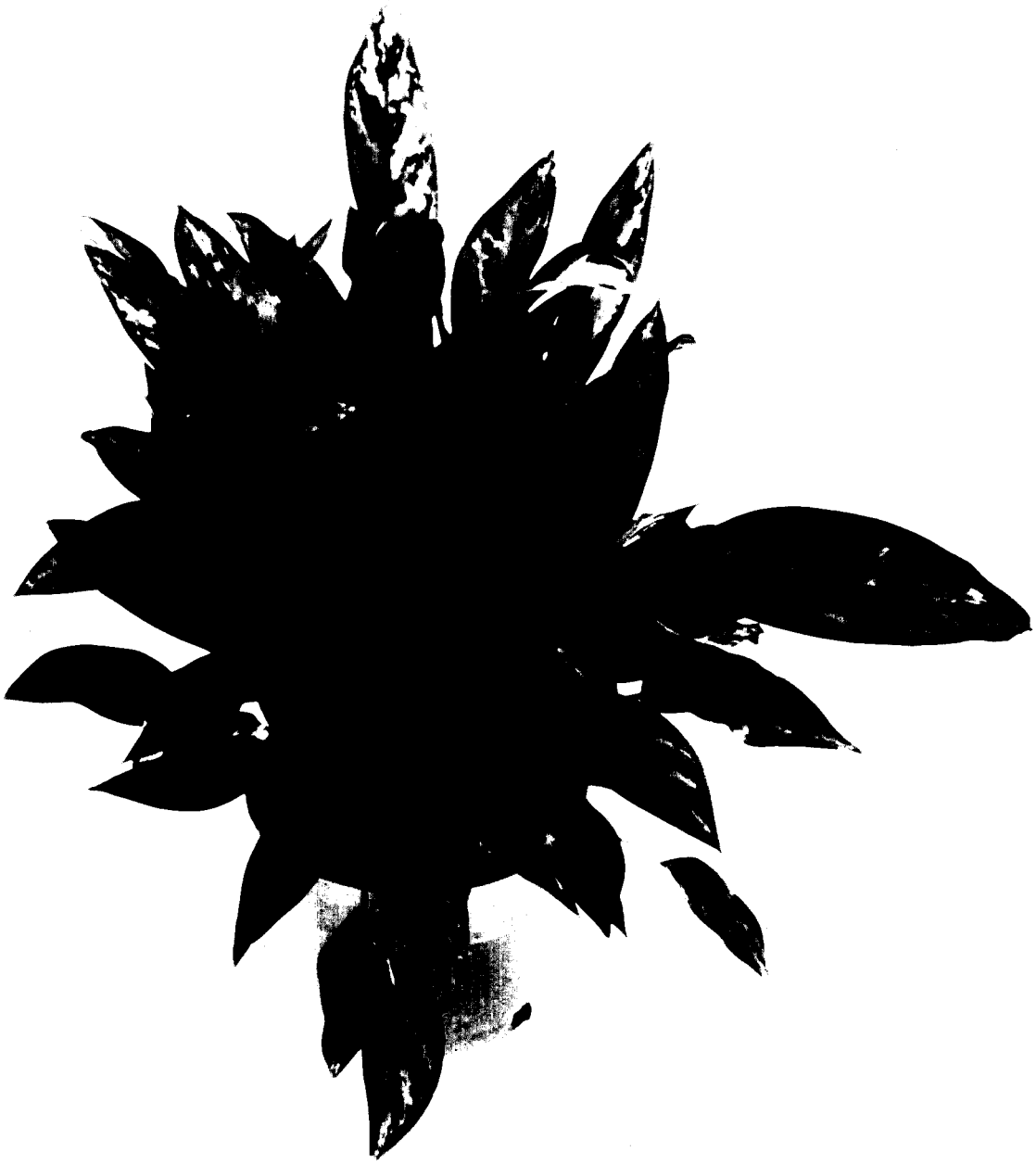

* * * * *